(12) United States Patent
Diaz et al.

(10) Patent No.: US 11,278,367 B1
(45) Date of Patent: Mar. 22, 2022

(54) PORTABLE AND COLLAPSIBLE APPARATUS FOR HOLDING FIDUCIAL MARKERS

(71) Applicant: The United States of America as Represented by the Secretary of the Navy, Indian Head, MD (US)

(72) Inventors: Angel Diaz, Indian Head, MD (US); David Rivera-Marchand, Alexandria, VA (US); Lonnie Frericks, King George, VA (US); Andrew Wojtkowski, Springfield, VA (US); Anthony Kummerer, LaPlata, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 203 days.

(21) Appl. No.: 16/602,554

(22) Filed: Oct. 31, 2019

(51) Int. Cl.
  *H05G 1/28* (2006.01)
  *A61B 50/22* (2016.01)
  (Continued)

(52) U.S. Cl.
  CPC .............. *A61B 50/22* (2016.02); *A61B 90/39* (2016.02); *G01N 23/04* (2013.01); *A61B 2090/3966* (2016.02); *G01N 2223/301* (2013.01)

(58) Field of Classification Search
  CPC . A61B 90/39; A61B 34/20; A61B 2090/3983; A61B 2034/2055; A61B 2090/3966; A61B 34/10; A61B 2034/107; A61B 2034/2051; A61B 2090/3937; A61B 2090/3945; A61B 2090/363; A61B 2090/365; A61B 34/30; A61B 2034/105; A61B 2034/2065; A61B 2090/378; A61B 90/37; A61B 90/02; A61B 18/1815; A61B 2018/00285; A61B 2018/00404; A61B 2018/00642; A61B 2018/183; A61B 2018/1861; A61B 2018/1884; A61B 2018/00023; A61B 2018/00351;
  (Continued)

(56) References Cited

U.S. PATENT DOCUMENTS 4,127,774 A * 11/1978 Gillen .................. G03B 42/047
                                                          378/162
4,426,723 A *  1/1984 Rouse .................. G03B 42/047
                                                          378/165
(Continued)

*Primary Examiner* — Irakli Kiknadze
(74) *Attorney, Agent, or Firm* — Fredric J. Zimmerman

(57) ABSTRACT

A portable and collapsible apparatus for holding fiducial markers has a first section that includes a frame, an opposite second side, a first panel attached to the first frame and fiducial markers attached to the first panel. The apparatus includes a second section pivotably attached to the first section and a second frame, an opposite second side, a second panel member attached to the second frame and fiducial markers attached to the second panel. The apparatus is configurable to a closed state by pivoting the first section and second section toward each other where the rear sides of the first frame and second frame contact each other. The apparatus is configurable to an opened state by pivoting the first section and second section away from each other. In the opened state, the first section and second section are vertically oriented with respect to a surface.

24 Claims, 6 Drawing Sheets

(51) Int. Cl.
*G01N 23/04* (2018.01)
*A61B 90/00* (2016.01)

(58) Field of Classification Search
CPC ........... A61B 2018/00577; A61B 2018/00714; A61B 3/0083; A61B 3/113; A61B 5/4023; A61B 5/4863; A61B 5/702; A61B 3/0025; A61B 3/102; A61B 3/1015; A61B 2034/2072; A61B 2090/376; A61B 3/103; A61B 3/107; A61B 3/14; A61B 2034/207; G06T 7/73; G06T 2207/30204; G06T 7/11; G06T 11/005; G06T 2207/10016; G06T 2211/436; G06T 7/0012; G06T 11/003; G06T 2207/10052; G06T 2207/10072; G06T 2207/10081; G06T 2207/10088; G06T 7/246; G06T 7/248; G06T 7/30; G06T 2207/10068; G06T 2207/10116; G06T 2207/10004; G06T 2207/30008; G06T 3/00; G06T 2207/30021; G06T 2207/30101; G06T 7/33; G06T 7/70; G06T 11/00; G06T 2207/10012; G06T 2207/30141; G06T 7/0008; G06T 15/08; G06T 15/20; G06T 19/006; G06T 2207/30012; G06T 7/74; G06T 17/00; G06T 17/20; G06T 2207/10132; G01B 11/24; G01B 11/245; G01B 11/25; G01B 7/003; G01B 9/02091; G01B 2290/65; G01B 7/004; G01B 9/02004; G01B 9/02028; G01B 9/02058; G01B 9/02069; H02J 2203/20; A61K 38/4886; A61K 38/49; G01T 1/161; G01T 1/29; G02B 27/017; H05G 1/025; G01N 23/04; G01N 23/043; G01N 15/05; G01N 1/4077; G01N 2001/4083; G01N 2009/026; G01N 33/491; G01N 9/02; A61N 5/1049; A61N 5/10; A61N 1/0534; A61N 1/36064; A61N 7/02; G01J 1/26; H01J 2237/2441; H01J 2237/24475; H01J 2237/3175; H01J 37/244
USPC .......................................... 378/163, 205–207
See application file for complete search history.

(56) References Cited

U.S. PATENT DOCUMENTS

| | | | | |
|---|---|---|---|---|
| 4,993,056 | A * | 2/1991 | Lary | A61B 10/0096 378/164 |
| 5,287,397 | A * | 2/1994 | Dumsha | G03B 42/047 30/363 |
| 6,626,569 | B2 * | 9/2003 | Reinstein | A61N 5/1048 250/252.1 |
| 7,027,644 | B1 | 4/2006 | Kim et al. | |
| 7,581,884 | B1 * | 9/2009 | Barnes | A61B 6/06 378/164 |
| 7,951,345 | B2 * | 5/2011 | Lary | G03B 42/04 422/561 |
| 8,111,808 | B1 | 2/2012 | Wood | |
| 8,411,820 | B1 | 4/2013 | Browder | |
| 8,548,563 | B2 | 10/2013 | Simon | |
| 9,002,062 | B2 | 4/2015 | Aller | |
| 9,129,427 | B2 | 9/2015 | Golubovec et al. | |
| 9,268,058 | B2 | 2/2016 | Peschmanet et al. | |
| 10,019,015 | B2 | 7/2018 | Johnson et al. | |
| 10,463,339 | B2 * | 11/2019 | Hilton | G01N 23/046 |
| 10,682,113 | B2 * | 6/2020 | Lin | A61B 90/39 |
| 2002/0105143 | A1 * | 8/2002 | Elliott | A63F 3/0023 273/285 |
| 2003/0095637 | A1 * | 5/2003 | Sabczynski | A61B 6/583 378/207 |
| 2008/0240364 | A1 * | 10/2008 | Main | A61N 5/1048 378/207 |
| 2009/0168958 | A1 * | 7/2009 | Cozzini | G01N 23/283 378/57 |
| 2010/0226478 | A1 * | 9/2010 | Harding | G21K 1/025 378/70 |
| 2012/0177182 | A1 * | 7/2012 | Olesinski | G01N 23/04 378/87 |
| 2020/0408510 | A1 * | 12/2020 | Drouin | G01S 17/89 |

* cited by examiner

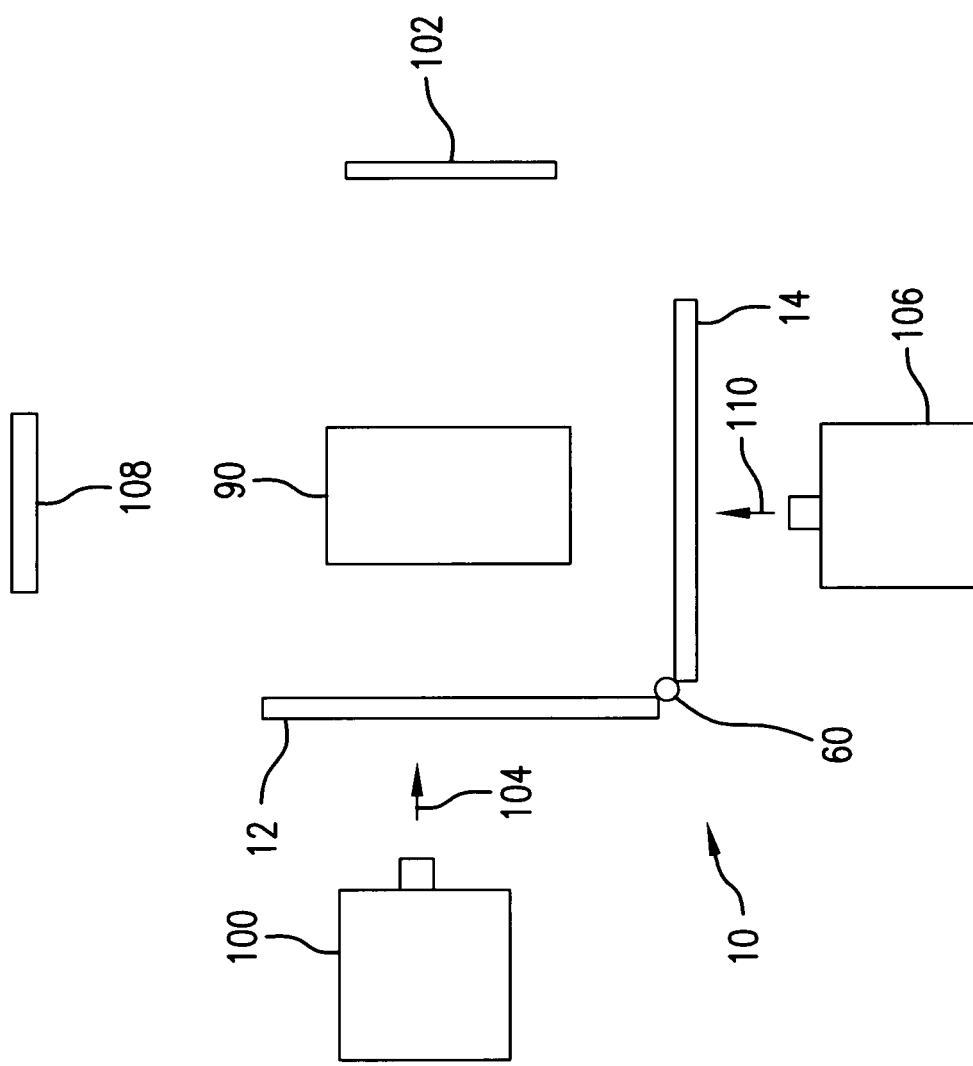

PORTABLE AND COLLAPSIBLE APPARATUS FOR HOLDING FIDUCIAL MARKERS

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

FIELD OF THE INVENTION

The present invention relates to a portable and collapsible apparatus for holding fiducial markers.

BACKGROUND

A fiducial marker is an object that is placed in the field of view of an imaging system. The fiducial marker appears in the image produced by the imaging system and is used as a point of reference or a measure. Fiducial markers are used in many industries and fields including, but not limited to, medicine, aerospace, optics and manufacturing. Conventional techniques using fiducial markers typically require that individual fiducial markers be positioned on or in a subject that is to undergo imaging. However, this technique is not practical or even feasible in the case of an enclosed opaque container that may contain a dangerous device, such as explosive material, an improvised explosive device (IED) or other energetic device. In many instances, individual fiducial markers are randomly positioned about the subject but the location of each fiducial marker in 3D space is not known thereby making difficult the determination of the orientation and location of objects within the interior of the enclosed opaque container.

What is needed is a fiducial marker apparatus that eliminates the aforementioned problems and disadvantages associated with conventional apparatuses, techniques and methods that utilize fiducial markers.

SUMMARY OF THE INVENTION

In one aspect, the present invention is directed to a portable and collapsible apparatus for holding fiducial markers. In an exemplary embodiment, the apparatus includes a first section comprising a first frame having a first side and an opposite second side, a low-reflectivity and low-density first panel attached to the first side of the first frame and a first plurality of fiducial markers attached or joined to the first panel and arranged in a first predetermined pattern. The apparatus further comprises a second section that is pivotably attached to the first section and which comprises a second frame having a first side and an opposite second side, a low-reflectivity and low-density second panel attached to the first side of the second frame and a second plurality of fiducial markers attached or joined to the second panel and arranged in a second predetermined pattern. The portable apparatus is configurable to a closed state by pivoting the first section and second section toward each other so that the second sides of the first frame and second frame contact each other. The portable apparatus is configurable to an opened state by pivoting the first section and second section away from each other, and wherein when the apparatus is in the opened state and placed on a surface, the first section and second section are vertically oriented with respect to the surface. In an exemplary embodiment, each fiducial marker comprises a tungsten disc. In an exemplary embodiment, each fiducial marker of the first plurality of fiducial markers is embedded in the first panel and each fiducial marker of the second plurality of fiducial markers is embedded in the second panel. In an exemplary embodiment, the apparatus includes a first handle attached to the first frame and a second handle attached to the second frame, wherein the first handle confronts the second handle when the apparatus is configured to the closed state thereby allowing a user to grasp the first handle and second handle simultaneously with one hand to facilitate transportation of the portable and collapsible apparatus. In an exemplary embodiment, the first pattern of the first plurality of fiducial markers is the same as the second pattern of the second plurality of fiducial markers.

Certain features and advantages of the present invention have been generally described in this summary section. However, additional features, advantages and embodiments are presented herein or will be apparent to one of ordinary skill of the art in view of the drawings, specification and claims hereof. Accordingly, it should be understood that the scope of the invention shall not be limited by the particular exemplary embodiments disclosed in this summary section.

BRIEF DESCRIPTION OF THE DRAWINGS

FIG. 6 is a diagram illustrating use of the portable and collapsible apparatus of the present invention with a pair of x-ray generating devices in order to image the interior of an enclosed opaque container.

DETAILED DESCRIPTION OF EXEMPLARY EMBODIMENTS OF THE INVENTION

As used herein, the terms "comprises", "comprising", "includes", "including", "has", "having" or any other variation thereof, are intended to cover a non-exclusive inclusion. For example, a process, method, article or apparatus that comprises a list of elements is not necessarily limited to only those elements, but may include other elements not expressly listed or inherent to such process, method, article or apparatus.

It is to be understood that throughout this description, terms such as "vertical", "horizontal", "top", "bottom", "upper", "lower", "middle", "above", "below" and the like are used for convenience in identifying relative locations of various components and surfaces relative to one another in reference to the drawings and are not intended to be limiting in any way.

As used herein, the term "computing resource" shall include desktop computers, notebook computers, laptop computers, mainframe computers, tablet computers, PDAs (Personal Digital Assistant), cloud computing and smart phones.

Approximating language, as used herein throughout the specification and claims, may be applied to modify any quantitative representation that could permissibly vary without resulting in a change in the basic function to which it is related. Accordingly, a value modified by a term such as "about" or "approximately" is not limited to the precise value specified.

Figure 1:
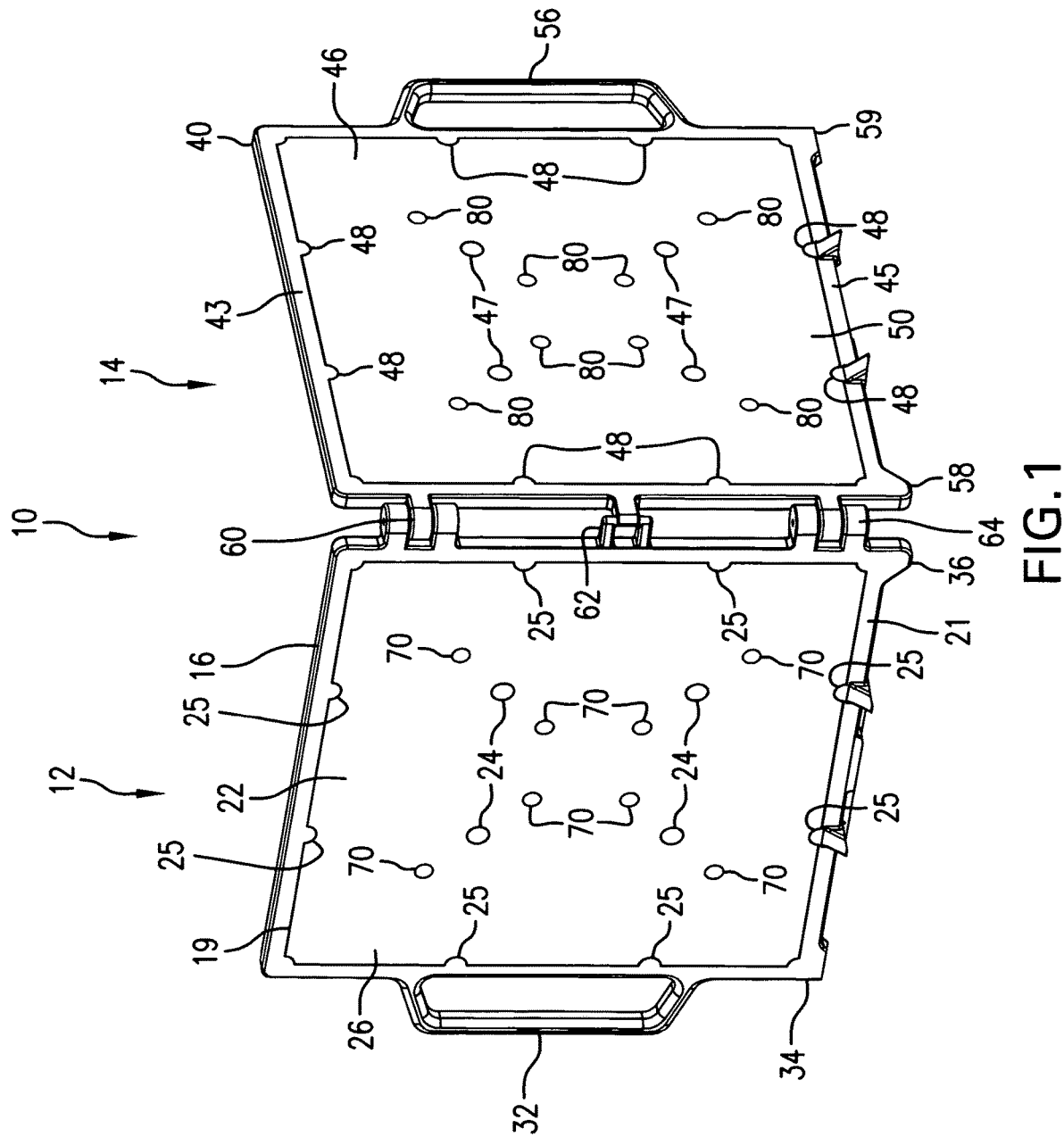
FIG. 1 is a perspective front view of a portable and collapsible apparatus for holding fiducial markers in accordance with an exemplary embodiment of the present invention.
Figure 2:
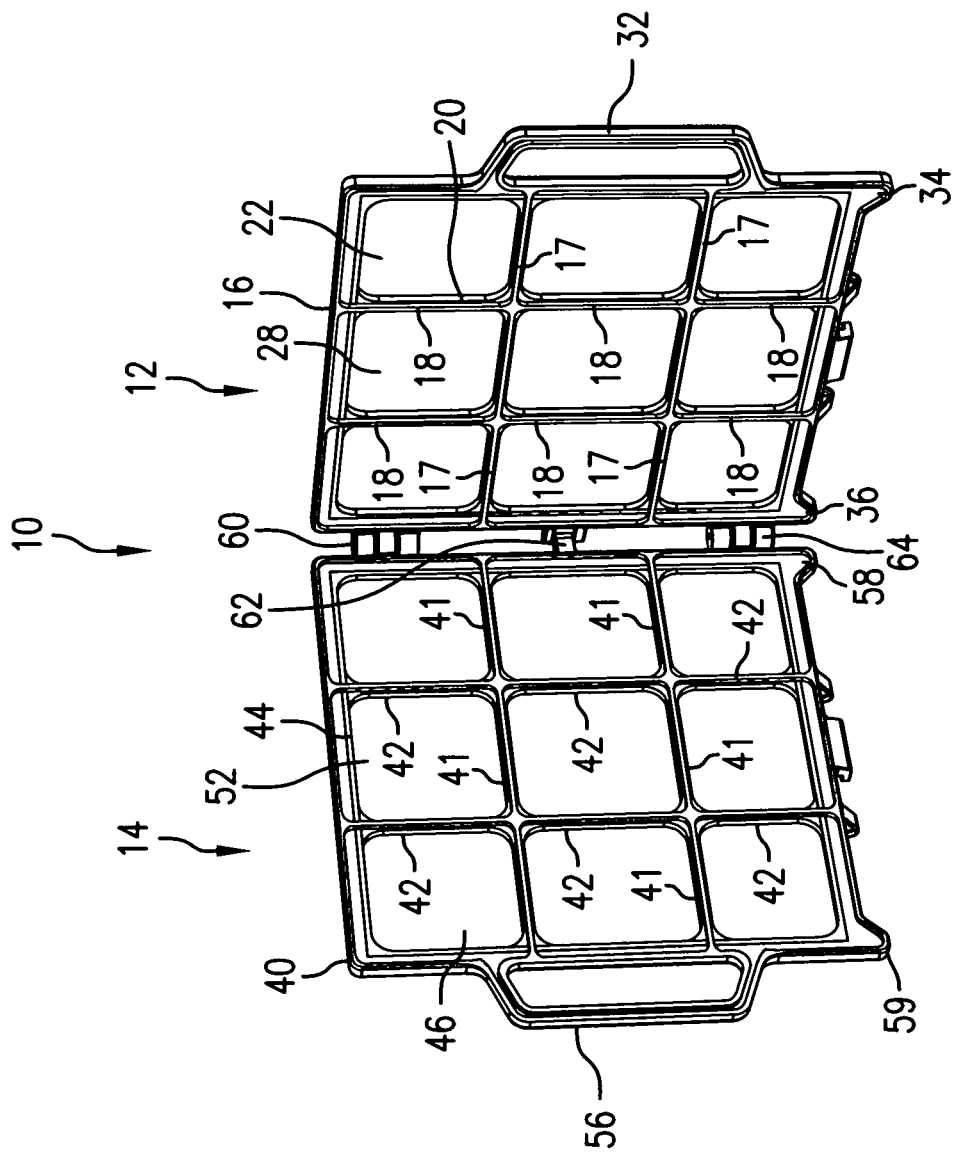
FIG. 2 is a perspective rear view of the portable and collapsible apparatus for holding fiducial markers.

Referring to FIGS. 1 and 2, there is shown portable and collapsible apparatus 10 for holding fiducial markers in accordance with an exemplary embodiment. Apparatus 10 comprises first section 12 and second section 14. First section 12 and second section 14 are movably attached to each other. This feature is discussed in detail in the ensuing description. First section 12 comprises frame 16 which includes horizontal structural support members 17 and vertical structural support members 18. Frame 16 has a first side 19 and opposite second side 20. Frame 16 further includes bottom portion or section 21. First section 12 includes panel member 22 that is attached to first side 19 of frame 16 such that panel member 22 physically contacts horizontal structural support members 17 and vertical structural support members 18. Panel member 22 includes openings that are sized to receive protruding members 24 that are attached to first side 19 of frame 16. In an exemplary embodiment, the aforementioned openings in panel member 22 are sized so that protruding members 24 frictional fit into the openings so that panel member 22 is firmly attached to first side 19 of frame 16 and does not exhibit any lateral movement while attached to first side 19. In an exemplary embodiment shown in FIG. 1, there are four protruding members 24. However, in other embodiments, there may be less than or more than four protruding members 24. Frame 16 further includes inwardly extending tab members 25 on first side 19 which retain panel member 22 against horizontal support members 17 and vertical support members 18. Each tab member 25 physically contacts a portion of panel member 22. Panel member 22 has front side 26 and rear side 28. In one exemplary embodiment, protruding members 24 do not extend beyond the thickness of panel member 22 such that the end of each protruding member 24 is substantially co-planar with the front side 26 of panel member 22. Panel member 22 is fabricated from a low-reflectivity and low-density material. In an exemplary embodiment, the low-reflectivity and low-density material is rugged and waterproof. In one embodiment, panel member 22 is fabricated from a low-reflectivity and low-density plastic sheet. In an exemplary embodiment, the plastic sheet has a thickness of about ⅛ inch. However, it is to be understood that the plastic sheet may have a thickness that is less than or more than ⅛ inch. Frame 16 includes handle 32. Frame 16 further includes protruding portions 34 and 36 that are configured to contact the surface upon which apparatus 10 is placed.

Referring to FIGS. 1 and 2, second section 14 comprises frame 40 which includes horizontal structural support members 41 and vertical structural support members 42. Frame 40 has first side 43 and opposite second side 44. Frame 40 includes bottom portion or section 45. Second section 14 includes panel member 46, which is attached to first side 43 of frame 40. Panel member 46 includes openings that are sized to receive protruding members 47 that are attached to first side 43 of frame 40. In an exemplary embodiment, the aforementioned openings in panel member 46 are sized so that protruding members 47 frictional fit into the openings so that panel member 46 is firmly attached to first side 43 of frame 40 and does not exhibit any lateral movement while attached to first side 43. In an exemplary embodiment, there are four protruding members 47. However, in other embodiments, there may be less than or more than four protruding members 47. Frame 40 further includes inwardly extending tab members 48 on first side 43, which retain panel member 46 against first side 43. Each tab member 48 physically contacts a portion of panel member 46. Panel member 46 has front side 50 and rear side 52. In an exemplary embodiment, protruding members 47 do not extend beyond the thickness of panel member 46 such that the outer surface of each protruding member 47 is substantially co-planar with the front side 50 of panel member 46. Panel member 46 is fabricated from a low-reflectivity and low-density material. In an exemplary embodiment, the low-reflectivity and low-density material is rugged and waterproof. In one embodiment, panel member 46 is fabricated from a low-reflectivity and low-density plastic sheet. In an exemplary embodiment, the plastic sheet has a thickness of about ⅛ inch. However, it is to be understood that the plastic sheet may have a thickness that is less than or more than ⅛ inch. As shown in FIG. 1, frame 40 includes handle 56. Frame 40 further includes protruding portions 58 and 59 that are configured to contact a surface upon which apparatus 10 is placed.

In an exemplary embodiment, first section 12 and second section 14 are pivotally or hingedly attached to each other via hinge assemblies 60, 62 and 64 so as to allow apparatus 10 to open and close like a book. Each hinge assembly 60, 62 and 64 comprises a first section that is attached to frame 16 of first section 12 and a second section that is attached to frame 40 of second section 14. Handles 32 and 56 allow a user to open apparatus 10 so that first section 12 and second section 14 are angulated with respect to each other. In an exemplary embodiment, first section 12 and second section 14 may be pivoted so that the degree of angulation between first section 12 and second section 14 is between 0° and 180°. When apparatus 10 is not in use, a user can grasp handles 32 and 56 and pivot first section 12 and second section 14 toward each other so as to close apparatus 10. When apparatus 10 is closed, handles 32 and 56 confront each other. In some embodiments, handles 32 and 56 contact each other when apparatus 10 is closed. Once handles 32 and 56 contact or confront each other, the user may grasp both handles 32 and 56 with a single hand in order to carry or transport apparatus 10.

Referring to FIGS. 1 and 2, first section 12 further comprises a plurality of fiducial markers 70 that are attached or joined to panel member 22. Fiducial markers 70 are separate markers and are not part of a grid. In some embodiments, fiducial markers 70 do not protrude beyond the surface of front side 26 of panel member 22. In some embodiments, fiducial markers 70 are joined or attached to panel member 22 in such a manner that fiducial markers 70 are visible only on front side 26 of panel member 22. In other embodiments, fiducial markers 70 are joined or attached to panel member 22 in such a manner that fiducial markers 70 are visible on both front side 26 and rear side 28 of panel member 22. In an exemplary embodiment, fiducial markers 70 are embedded in panel member 22. Fiducial markers 70 are arranged in a predetermined pattern. In an exemplary embodiment, there are eight fiducial markers 70 that are arranged in an "X" pattern. However, in some embodiments, fiducial markers 70 are arranged in different patterns. For example, in some embodiments, fiducial markers 70 are arranged in columns and rows. In an exemplary embodiment, each fiducial marker 70 comprises a tungsten disc. In other embodiments, fiducial markers 70 are fabricated from other suitable materials including, but not limited to, gold, carbon, polymer, nitinol and zirconium oxide covered by pyrolytic carbon. The quantity and shape of fiducials markers 70 may be varied in other embodiments.

Referring to FIGS. 1 and 2, second section 14 further comprises a plurality of fiducial markers 80 that are attached or joined to panel member 46. Fiducial markers 80 are separate markers and are not part of a grid. In some embodiments, fiducial markers 80 do not protrude beyond the surface of front side 50 of panel member 46. In some embodiments, fiducial markers 80 are joined or attached to panel member 46 in such a manner that fiducial markers 80 are visible only on front side 50 of panel member 46. In other embodiments, fiducial markers 80 are joined or attached to panel member 46 in such a manner that fiducial markers 80 are visible on both front side 50 and rear side 52 of panel member 46. In an exemplary embodiment, fiducial markers 80 are embedded in panel member 46. Fiducial markers 80 are arranged in a predetermined pattern. In an exemplary embodiment, there are eight fiducial markers 80 that are arranged in an "X" pattern. In other embodiments, fiducial markers 80 are arranged in different patterns. For example, in some embodiments, fiducial markers 80 are arranged in columns and rows. In an exemplary embodiment, each fiducial marker 80 comprises a tungsten disc. In other embodiments, fiducial markers 80 are fabricated from other suitable materials including, but not limited to, gold, carbon, polymer, nitinol and zirconium oxide covered by pyrolytic carbon. The quantity and shape of fiducials markers 80 may be varied in other embodiments.

Fiducial markers 70 and 80 are used as reference points when taking x-rays of an object. This is illustrated in FIG. 6. It is desired to determine the contents of enclosed opaque container 90. Apparatus 10 is opened so that second section 14 is pivoted 90° from first section 12. Apparatus 10 is then positioned adjacent to enclosed opaque container 90 so that first section 12 faces one side of enclosed opaque container 90 and second section 14 faces another side of enclosed opaque container 90. First x-ray machine 100 is positioned so that it faces front side 26 of panel member 22. In this configuration, x-ray radiation emitted by x-ray machine 100 is directed to front side 26 of panel member 22. First x-ray film 102 is positioned on the opposite side of enclosed opaque container 90 such that enclosed opaque container 90 is positioned between first section 12 and first x-ray film 102. In an exemplary embodiment, first x-ray film 102 is aligned with and substantially parallel to first section 12. Next, the first-x-ray is taken such that first x-ray radiation 104 passes through first section 12, enclosed opaque container 90 and first x-ray film 102 thereby providing a first x-ray image. Fiducial markers 70 appear on the first x-ray image along with a view of the contents of enclosed opaque container 90 as seen from that angle. Second x-ray machine 106 is positioned so that it faces front side 50 of panel member 46. In this configuration, x-ray radiation emitted by x-ray machine 106 is directed to front side 50 of panel member 46. Second x-ray film 108 is positioned on the opposite side of enclosed opaque container 90 such that enclosed opaque container 90 is positioned between second section 14 and second x-ray film 108. In an exemplary embodiment, second x-ray film 108 is aligned with and substantially parallel to second section 14. Next, the second x-ray is taken such that second x-ray radiation 110 passes through second section 14, enclosed opaque container 90 and second x-ray film 108 thereby providing a second x-ray image. Fiducial markers 80 appear on the second x-ray image along with a view of the contents of enclosed opaque container 90 as seen from that angle.

The first x-ray image and second x-ray image may be scanned via digital scanner in order to digitize the first x-ray image and the second x-ray image to produce digital x-ray images of the interior of enclosed opaque container 90 from two different angles. In an exemplary embodiment, the digital x-ray images may be in any one of a variety of file formats including JPEG, PDF, PNG, GIF, TIFF, etc. The digital x-ray images may be exported to a computing resource with a display screen that can display the digital x-ray images.

Figure 3:
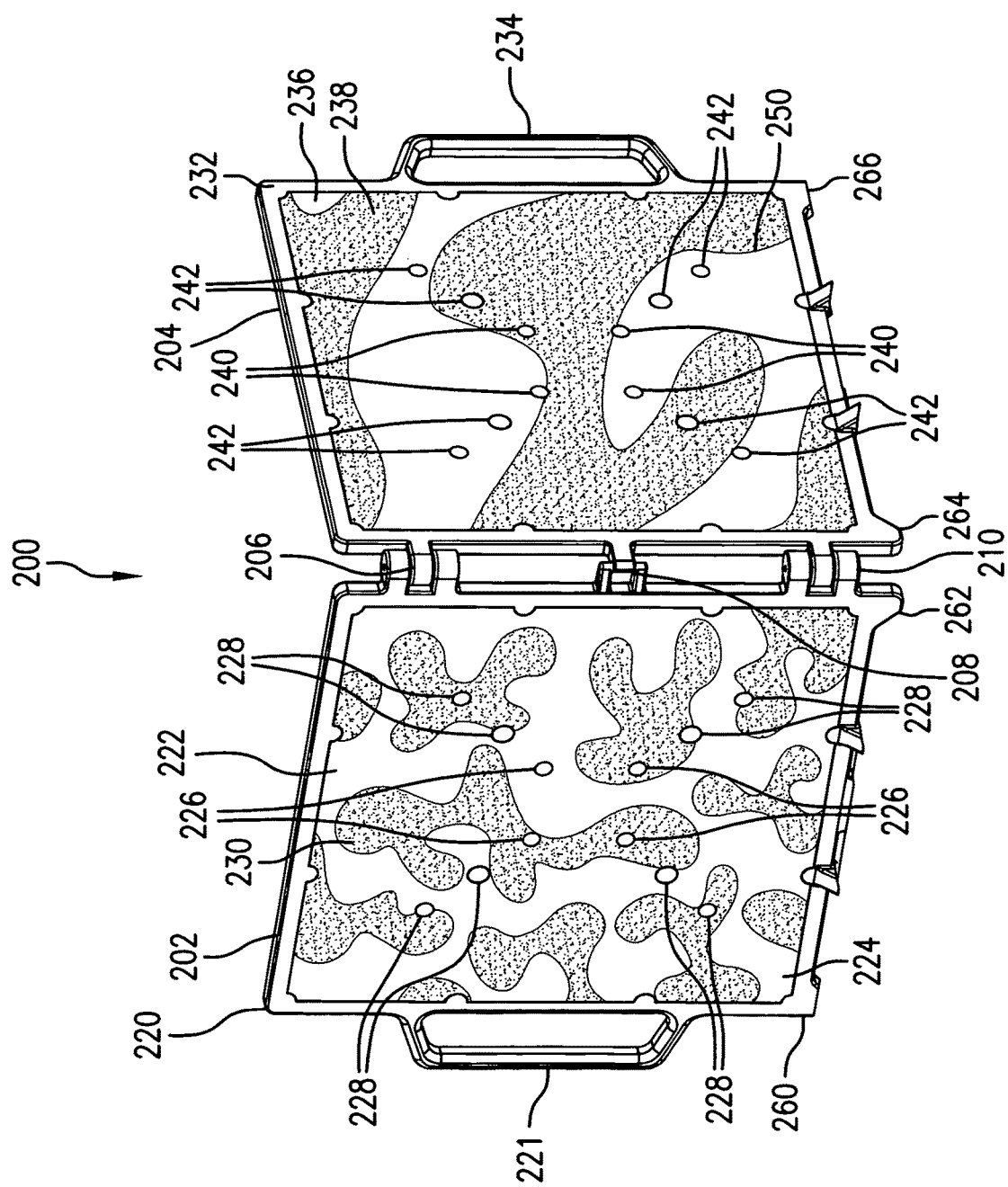
FIG. 3 is a perspective front view of a portable and collapsible apparatus for holding fiducial markers in accordance with another exemplary embodiment of the present invention.

Referring to FIG. 3, there is shown portable and collapsible apparatus 200 for holding fiducial markers in accordance with another exemplary embodiment. As will be described in the ensuing description, apparatus 200 is configured for applications relating to augmented and virtual reality. Apparatus 200 comprises first section 202 and second section 204. First section 202 and second section 204 are movably attached to each other in the same manner as first section 12 and second section 14 of apparatus 10. Apparatus 200 includes hinge assemblies 206, 208 and 210, which have the same structure and function as hinge assemblies 60, 62 and 64, respectively, of apparatus 10. First section 202 comprises frame 220, which has the same structure and function as frame 16 of first section 12 of apparatus 10. Frame 220 further comprises handle 221 and panel member 222. Panel member 222 may be fabricated from the same low-reflectivity and low-density materials from which panel members 22 and 46 are fabricated (see FIG. 1). Panel member 222 includes front side 224 and an opposite second side (not shown). Frame 220 includes protruding members 226 that frictionally fit into corresponding openings in panel member 222 so as to secure panel member 222 to frame 220. Protruding members 226 have the same structure and function as protruding members 24 and 47 that were described in the foregoing description. Apparatus 200 further comprises a plurality of fiducial markers 228 that are attached or joined to panel member 222. In an exemplary embodiment, each fiducial marker 228 is in the shape of a disc and is fabricated from any of the materials described in the foregoing description with respect to fiducial markers 70 and 80. Fiducial markers 228 are separate markers and are not part of a grid. In an exemplary embodiment, fiducial markers 228 are joined or attached to panel member 222 in such a manner that the fiducial markers 228 are visible only on front side 224 of panel member 222. In some embodiments, fiducial markers 228 are joined or attached to panel member 222 in such a manner that the fiducial markers 228 are visible on both front side 224 and the rear side of panel member 222. In an exemplary embodiment, fiducial markers 228 are embedded in panel member 222. Panel member 222 includes predefined image 230 that is formed on front side 224. Image 230 is only visible on front side 224. Image 230 has a unique pattern or design. The characteristics and purpose of image 230 are described in the ensuing description.

Referring to FIG. 3, second section 204 comprises frame 232 which has the same structure and function as frame 40 of second section 14 (see FIG. 1). Frame 232 further comprises handle 234 and panel member 236. Panel member 236 may be fabricated from the same low-reflectivity and low-density materials from which panel members 22 and 46

(see FIG. 1) are fabricated. Panel member 236 includes front side 238 and an opposite rear side (not shown). Frame 232 includes protruding members 240 that frictionally fit into corresponding openings in panel member 236 so as to secure panel member 236 to frame 232. Protruding members 240 have the same structure and function as protruding members 24 and 47 described in the foregoing description. Apparatus 200 further comprises a plurality of fiducial markers 242 that are attached or joined to panel member 236. In an exemplary embodiment, each fiducial marker 242 is in the shape of a disc and is fabricated from any of the suitable materials described herein with respect to fiducial markers 70 and 80. Fiducial markers 242 are separate markers and are not part of a grid. In an exemplary embodiment, fiducial markers 242 are joined or attached to panel member 236 in such a manner that the fiducial markers 242 are visible only on front side 238 of panel member 236. In some embodiments, fiducial markers 242 are joined or attached to panel member 236 in such a manner that the fiducial markers 242 are visible on both front side 238 and the rear side of panel member 236. In an exemplary embodiment, fiducial markers 242 are embedded in panel member 236. Panel member 236 includes predefined image 250 that is formed on front side 238. Image 250 has a unique pattern or design that is different than the pattern or design of image 230. Image 250 is only visible on front side 238. The characteristics and purpose of pattern 250 are described in the ensuing description.

Referring to FIG. 3, frame 220 includes protruding portions 260 and 262 that are configured for placement on the surface upon which apparatus 200 is placed. Frame 232 includes protruding portions 264 and 266 that are configured for placement on the surface upon which apparatus 200 is placed.

Referring to FIG. 3, patterns 230 and 250 are formed or fabricated with low-reflectivity and low-density material that will not appear on x-ray images. Examples of low-reflectivity and low-density materials include, but are not limited to, plastics, polymers, foams and ceramics. In an exemplary embodiment, images 230 and 250 have a "camouflage" design or pattern. However, it is to be understood that images 230 and 250 may have other types of designs or patterns. In an exemplary embodiment, the patterns of images 230 and 250 are random patterns. In one embodiment, these random patterns are created by suitable image creation software or raster graphics editor software that is configured to graphically design, create and edit images. The user sets or predefines the height and width of the images using the image creation software. Suitable image creation software includes, but is not limited to, Adobe® Photoshop, Adobe® Illustrator, Fatpaint® DrawPlus™, InkScape™ and Ultimate Paint™. Once images 230 and 250 are created, the images 230 and 250 are engraved onto panel members 222 and 236, respectively, using a laser-engraver. For example, if each panel member 222 and 236 is made from a low-reflectivity and low-density plastic sheet, then each image 230 and 250 is engraved onto one side of a corresponding plastic sheet with a low-reflectivity and low-density material. In an exemplary embodiment, the thickness of image 230 is substantially the same as the thickness of image 250.

The completed images 230 and 250 and their dimensions are processed with one or more commercially available algorithms in order to generate a data set for each image 230 and 250. In one exemplary embodiment, a computing resource is used to process images 230 and 250 and the corresponding dimensions to generate the data set for each image 230 and 250. In another exemplary embodiment, images 230 and 250 and their corresponding dimensions are fed or inputted into a commercial-off-the-shelf (COTS) online algorithm that generates the data set for each image 230 and 250. The data sets are used to create or generate virtual depictions of image 230 and 250. The generated virtual depictions of images 230 and 250 are to be used as part of a virtual reality environment that is displayed on a display screen of a computing resource. The virtual reality environment will include virtual depictions of fiducial markers 228 and 242, and the interior of enclosed opaque container 90. Since the data sets are stored in a memory medium (e.g. ROM, EPROM, RAM, etc.) in the computing resource, images 230 and 250 are recognized by a programmable image capturing device (e.g. programmable digital camera system) programmed with machine vision software and which is in electronic data signal communication with the computing resource. An example of machine vision software is Advanced Computer Vision (ACV) Software. An example of a programmable image capturing device is a smart phone camera that is programmed with a machine vision software App. Thus, fiducial markers 228 and 242 cooperate with images 230 and 250, respectively, to serve as real world anchors of location, orientation and scale of objects within the interior of enclosed opaque container 90.

Figure 4:
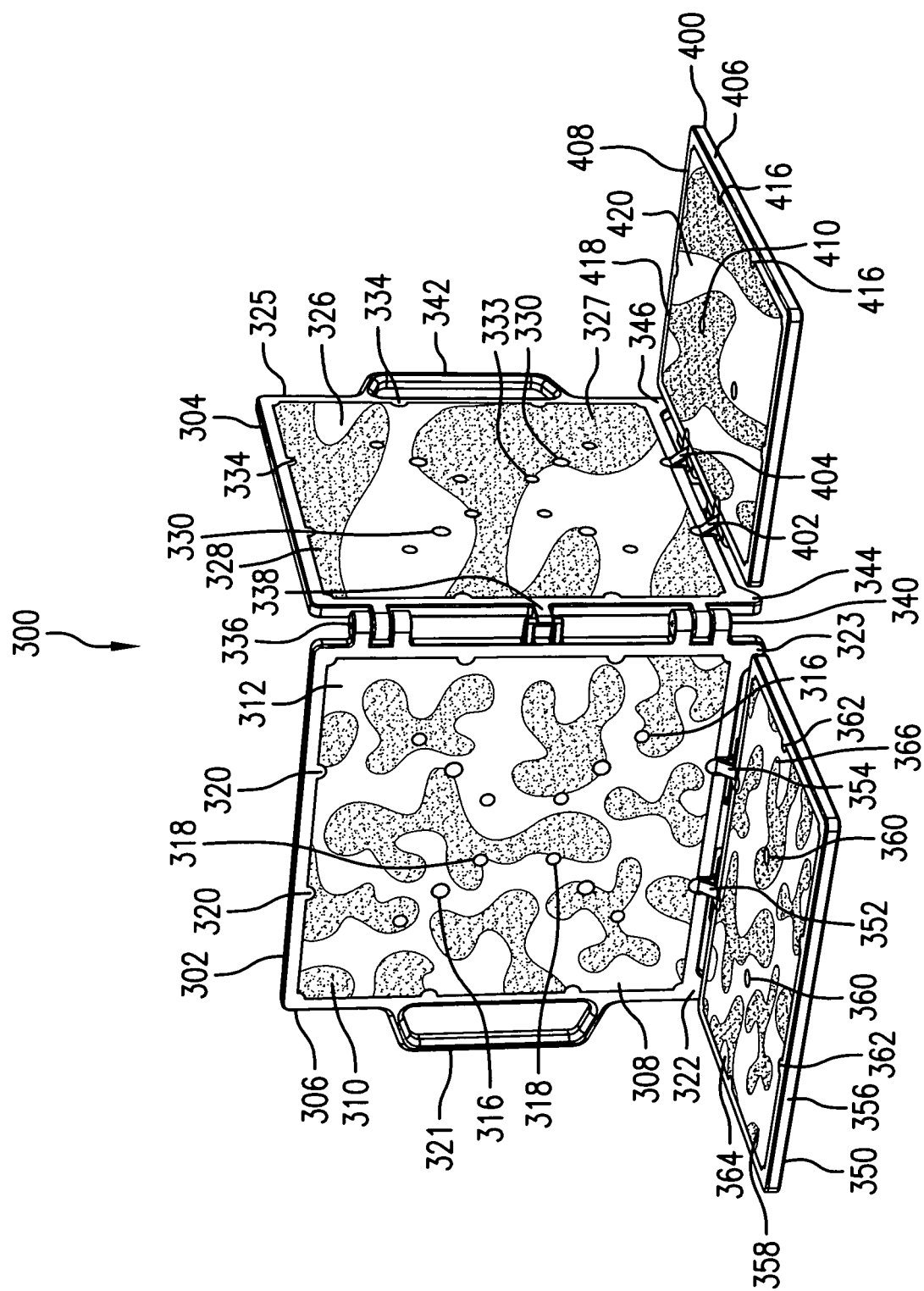
FIG. 4 is perspective front view of a portable and collapsible apparatus for holding fiducial markers in accordance with a further exemplary embodiment of the present invention.

Referring to FIG. 4, there is shown portable and collapsible apparatus 300 for holding fiducial markers. Apparatus 300 comprises first section 302 and second section 304. The structure and function of first section 302 are identical to the structure and function of first section 202 (see FIG. 3). Therefore, for purposes of simplifying the drawing, not every element of first section 302 is indicated by a reference number. First section 302 comprises frame 306, panel member 308 that is attached to frame 306, image 310 that is formed on front side 312 of panel member 308, and a plurality of fiducial markers 316 that are joined or attached to panel member 308. Frame 306 includes a plurality of protruding members 318 that provide the same function as protruding members 226 (see FIG. 3). Frame 306 has a plurality of inwardly extending tabs 320 that retain panel member 308 in place. Image 310 is substantially the same as image 230 shown in FIG. 3 and provides the same function as image 230. Frame 306 includes handle 321 and protruding portions 322 and 323. Protruding portions 322 and 323 are configured to contact the surface upon which apparatus 300 is placed.

Referring to FIG. 4, the structure and function of second section 304 are identical to the structure and function of second section 204 (see FIG. 3). Therefore, for purposes of simplifying the drawing, not every element of second section 304 is indicated by a reference number. Second section 304 comprises frame 325, panel member 326 that is attached to frame 325, image 327 that is formed on front side 328 of panel member 326 and a plurality of fiducial markers 330 that are joined or attached to panel member 327. Image 327 may be formed with the same low-reflectivity and low-density material from which patterns 230 and 250 are formed. The pattern or design of image 327 is substantially the same as the pattern of image 250 (see FIG. 3) and provides the same function as image 250. The pattern or design of image 327 is different than the pattern or design of image 310.

Frame 325 includes protruding members 333 that provide the same function as that of protruding members 240 (see FIG. 3). Frame 325 includes a plurality of inwardly extending tabs 334 that retain panel member 326 in place. First section 302 and second section 304 are pivotably attached together via hinge assemblies 336, 338 and 340. Each hinge assembly 336, 338 and 340 includes a first section that is attached to frame 306 of first section 302 and a second section that is attached to frame 325 of second section 304. Frame 325 includes handle 342 and protruding portions 344 and 346 that are configured to contact the surface upon which apparatus 300 is placed.

Apparatus 300 further comprises third section 350 that is pivotably attached to the bottom portion of frame 306 via hinge assemblies 352 and 354 so that third section 350 can pivot toward or away from first section 302. Specifically, hinge assemblies 352 and 354 allow that third section 350 to pivot toward or away from front side 312 of panel member 308. Third section 350 comprises frame 356 and panel member 358, which is attached to frame 356. Frame 356 includes protruding members 360 that provide the same function as protruding members 318 and are sized to fit into corresponding openings in panel member 358. Each hinge assembly 352 and 354 has a first section that is attached to frame 306 and a second section that is attached to frame 356. Frame 356 includes inwardly extending tabs 362 that retain panel member 358 in place. Panel member 358 includes front side 364 and an opposite rear side (not shown). Image 366 is formed on front side 364 and may be fabricated from the same low-reflectivity and low-density material from which patterns 230 and 250 are fabricated. The pattern of image 366 is different than the patterns of images 310 and 327.

Apparatus 300 further comprises fourth section 400 that is pivotably attached to the bottom portion of frame 325 via hinge assemblies 402 and 404 so that fourth section 400 can pivot toward or away from second section 304. Specifically, hinge assemblies 402 and 404 allow fourth section 400 to pivot toward or away from front side 328 of panel member 326. Fourth section 400 comprises frame 406 and panel member 408, which is attached to frame 406. Frame 406 includes protruding members 410 that provide the same function as protruding members 333 and are sized to fit into corresponding openings in panel member 408. Each hinge assembly 402 and 404 has a first section that is attached to the bottom portion of frame 325 and a second section that attached to frame 406. Frame 406 includes inwardly extending tabs 416 that retain panel member 408 in place. Panel member 408 includes front side 418 and an opposite rear side (not shown). Image 420 is formed on front side 418 of panel 408. Image 420 may be formed from the same low-reflectivity and low-density material from which images 230 and 250 are formed. The pattern or design of image 420 is different than the patterns or designs of images of 310, 327 and 366.

As shown in FIG. 4, when apparatus 300 is in the opened state and placed on a surface such as a floor or table top, first section 302 and second section 304 are vertically oriented with respect to the surface, third section 350 is horizontally oriented and substantially perpendicular to first section 302 and positioned flat upon the surface, and fourth section 400 is horizontally oriented and substantially perpendicular to second section 304 and positioned flat upon the surface. Images 366 and 420 provide additional reference points if an image capturing device (e.g. programmable digital camera system) is positioned above apparatus 300 and enclosed opaque container 90. If the image capturing device were positioned directly above apparatus 300, the only portions of first section 302 and second section 304 that would be visible would be the top edges of first section 302 and second section 304. However, since third section 350 and fourth section 400 are horizontally oriented, images 366 and 420 would be captured by the image capturing device. If data defining images 366 and 420 is stored in a computing resource, then the machine vision software of the image capturing device would recognize images 366 and 420. Thus, the additional reference points provided by images 366 and 420 can be used to locate and orient objects or items inside enclosed opaque container 90.

Figure 5:
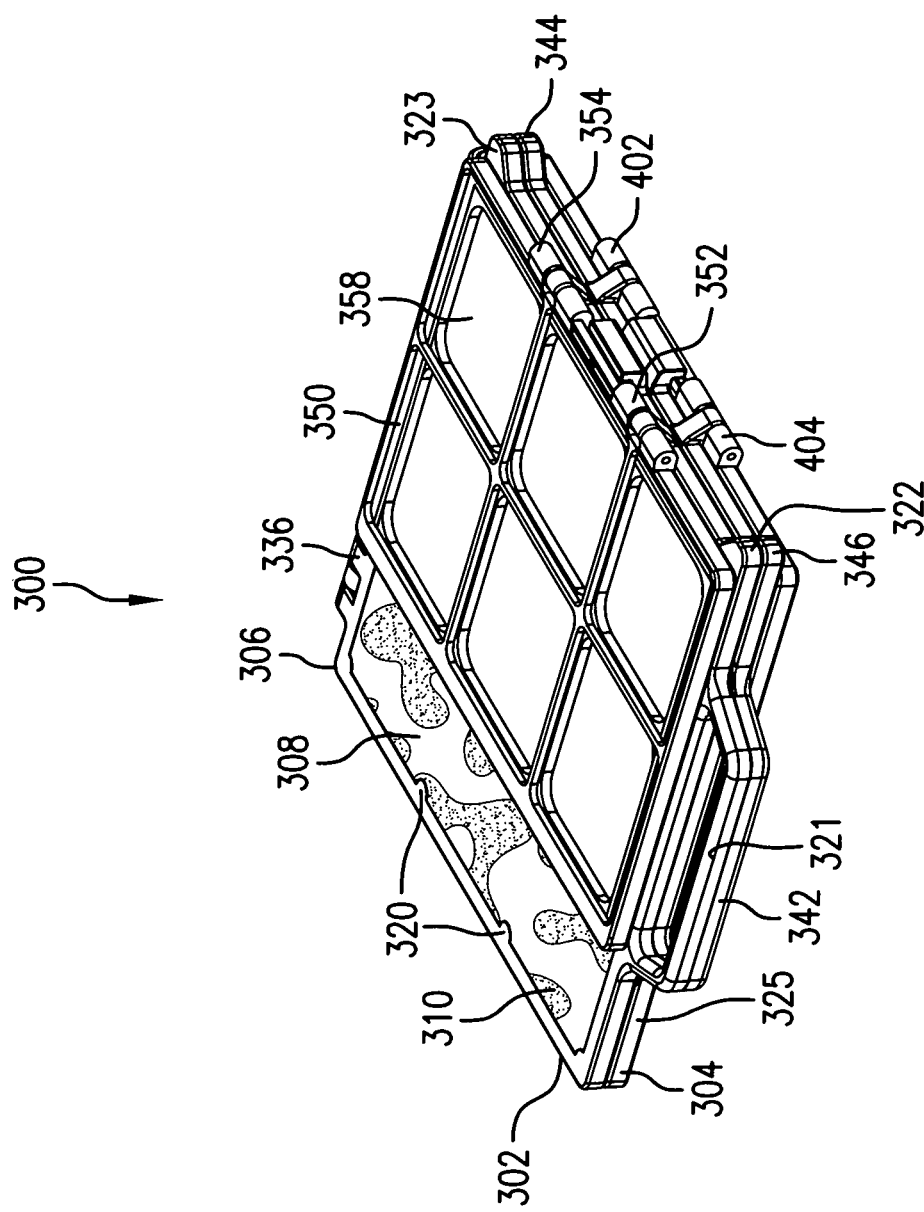
FIG. 5 is a perspective view showing the portable and collapsible apparatus of FIG. 4 in a folded state.

Hinge assemblies 336, 338, 340, 352, 354, 402 and 404 allow apparatus 300 to be collapsed and folded as shown in FIG. 5 to facilitate carrying, transporting and storing apparatus 300.

Frames 16, 40, 220, 232, 306, 325, 356 and 406 may be fabricated from any one of a variety of suitable materials including, but not limited to, plastic, rubber, resin, Plexiglas, Polyvinylchloride (PVC) and composite materials.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

Reference in the specification to "an exemplary embodiment", "one embodiment", "an embodiment", "some embodiments" or "other embodiments" means that a particular feature, structure or characteristic described in connection with the embodiment is included in at least one embodiment of the invention. The appearances of the phrases "an exemplary embodiment", "one embodiment", "an embodiment", "some embodiments" or "other embodiments" in various places in the specification are not necessarily all referring to the same embodiment.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. A portable and collapsible apparatus for holding fiducial markers, comprising:
   a first section comprising a first frame having a first side and an opposite second side, a low-reflectivity and low-density first panel being attached to the first side of the first frame and a first plurality of fiducial markers being attached to the first panel and being arranged in a first pattern;
   a second section being pivotably attached to the first section and comprising a second frame having a first side and an opposite second side, a low-reflectivity and low-density second panel attached to the first side of the second frame and a second plurality of fiducial markers attached to the second panel and arranged in a second pattern,
   wherein the apparatus is configurable to a closed state by pivoting the first section and second section toward each other so that the second sides of the first frame and second frame contact each other, wherein the apparatus is configurable to an opened state by pivoting the first section and second section away from each other, and wherein when the apparatus is in the opened state and placed on a surface, the first section and second section are vertically oriented with respect to the surface; and a third section being pivotably attached to the first frame such that the third section is pivotable toward or away from the front side of the first panel, wherein when the apparatus is in the opened state and placed on a surface such that the first section and second section are vertically oriented with respect to the surface, the third section is horizontally oriented, substantially perpendicular to the first section and positioned flat upon the surface.

2. The apparatus according to claim 1, wherein each fiducial marker is a disc shaped fiducial marker.

3. The apparatus according to claim 1, wherein each fiducial marker is fabricated from a material chosen from the group consisting of tungsten, gold, carbon, polymer and nitinol.

4. The apparatus according to claim 1, wherein the first section and the second section are pivotable so that the degree of angulation between the first section and the second section is between 0° and 180°.

5. The apparatus according to claim 1, wherein the first section and second section are pivotable so that the degree of angulation between the first section and the second section is 90°.

6. The apparatus according to claim 1, further comprising at least one hinge assembly, wherein each said hinge assembly comprises a first portion attached to the first frame of the first section and a second portion attached to the second frame of the second section.

7. The apparatus according to claim 1, further comprising a first handle being attached to the first frame and a second handle attached to the second frame, wherein the first handle confronts the second handle when the apparatus is configured to the closed state.

8. The apparatus according to claim 1, wherein the first pattern of the first plurality of fiducial markers is the same as the second pattern of the second plurality of fiducial markers.

9. The apparatus according to claim 1, wherein the first plurality of fiducial markers are embedded in the first panel and the second plurality of fiducial markers are embedded in the second panel.

10. The apparatus according to claim 1, wherein the low-reflectivity and low-density first panel comprises a plastic sheet.

11. The apparatus according to claim 1, wherein the low-reflectivity and low-density second panel comprises a plastic sheet.

12. The apparatus according to claim 1, wherein the first frame and the second frame each include protruding portions configured to contact the surface upon which the apparatus is placed when the apparatus configured to the open state.

13. The apparatus according to claim 1, wherein the first side of the first frame includes a plurality of tab members to retain the first panel against the first side of the first frame.

14. The apparatus according to claim 13, wherein the first panel comprises a plurality openings, wherein the first frame comprises a plurality of protruding members on the first side thereof, and wherein each of the plurality of the protruding member is configured to fit within a corresponding opening in the first panel.

15. The apparatus according to claim 1, wherein the first side of the second frame includes a plurality of tab members to retain the second panel against the first side of the second frame.

16. The apparatus according to claim 15, wherein the second panel comprises a plurality openings, wherein the second frame comprises a plurality of protruding members on the first side thereof, and wherein each of the plurality of the protruding member is configured to fit within a corresponding opening in the second panel.

17. The apparatus according to claim 1, wherein the first panel comprises a front side and a rear side that faces the first side of the first frame, wherein the first panel includes a first image formed on the front side of the first panel with a low-reflectivity and low-density material, and wherein the first image incudes a unique pattern.

18. The apparatus according to claim 17, wherein the unique pattern is a random pattern.

19. The apparatus according to claim 1, wherein the second panel comprises a front side and a rear side that faces the first side of the second frame, wherein the second panel includes a second image formed on the front side of the second panel with a low-reflectivity and low-density material, and wherein the second image includes a unique pattern distinct from the pattern of the first image.

20. The apparatus according to claim 19, wherein the unique pattern of the second image is a random pattern.

21. The apparatus according to claim 1, wherein the third section comprises a third frame having a first side and an opposite second side, wherein the opposite second side faces the surface when the third section is positioned upon the surface, wherein the third frame comprises a low-reflectivity and low-density third panel having a front side and rear side attached to the first side of the third frame, wherein the third panel includes a third image formed on the front side of the third panel with a low-reflectivity and low-density material, and wherein the third image has a unique pattern or design.

22. The apparatus according to claim 1, further comprising a fourth section being pivotably attached to the second frame such that the fourth section is pivotable toward or away from the front side of the second panel, wherein when the apparatus is in the opened state and placed on a surface such that the first section and second section are vertically oriented with respect to the surface, the fourth section is horizontally oriented, substantially perpendicular to the second section and positioned flat upon the surface.

23. The apparatus according to claim 22, wherein the fourth section comprises a fourth frame having a first side and an opposite second side, wherein the opposite second side faces the surface when the fourth section is positioned flat upon the surface, wherein the fourth frame comprises a low-reflectivity and low-density fourth panel having a front side and rear side that is attached to the first side of the fourth frame, wherein the fourth panel includes a fourth image formed on the front side of the fourth panel with a low-reflectivity and low-density material, and wherein the fourth image has a unique pattern.

24. The apparatus according to claim 1, wherein the first frame and second frame are fabricated from a material chosen from the group consisting of plastic, rubber, resin, Plexiglas, Polyvinylchloride (PVC) and composite materials.

* * * * *